(12) United States Patent
Gorsuch et al.

(10) Patent No.: US 7,572,374 B2
(45) Date of Patent: *Aug. 11, 2009

(54) ANTICOAGULANT AND THROMBO-RESISTANT HOLLOW FIBER MEMBRANES FOR IN-VIVO PLASMAPHERESIS AND ULTRAFILTRATION

(75) Inventors: Reynolds G. Gorsuch, Yountville, CA (US); Harold H. Handley, Jr., Encinitas, CA (US); Harold W. Peters, Martinez, CA (US); Jacob C. Kearns, Martinez, CA (US)

(73) Assignee: Transvivo, Inc., Napa, CA (US)

( * ) Notice: Subject to any disclaimer, the term of this patent is extended or adjusted under 35 U.S.C. 154(b) by 654 days.

This patent is subject to a terminal disclaimer.

(21) Appl. No.: 11/334,994

(22) Filed: Jan. 18, 2006

(65) Prior Publication Data

US 2006/0124530 A1 Jun. 15, 2006

Related U.S. Application Data

(60) Continuation-in-part of application No. 10/959,918, filed on Oct. 6, 2004, now Pat. No. 7,195,711, which is a continuation-in-part of application No. 10/666,185, filed on Sep. 17, 2003, now Pat. No. 6,802,971, which is a division of application No. 09/549,131, filed on Apr. 13, 2000, now Pat. No. 6,802,820.

(51) Int. Cl.
*B01D 63/02* (2006.01)
*B01D 69/08* (2006.01)
*B01D 71/68* (2006.01)

(52) U.S. Cl. .......... 210/500.23; 210/483; 210/490; 210/491; 210/500.41; 422/44; 604/6.04; 604/6.09

(58) Field of Classification Search .......... 210/600, 210/634, 644, 645, 646, 650, 651, 195.2, 210/200, 203, 483, 488, 490, 491, 500.1, 210/500.21, 500.23, 500.24, 500.41, 503, 210/504, 505, 506, 508; 422/44; 604/4.01, 604/5.01, 6.04, 6.09, 27
See application file for complete search history.

(56) References Cited

U.S. PATENT DOCUMENTS

| | | | |
|---|---|---|---|
| 3,494,121 A | 2/1970 | Bohrer | |
| 4,832,034 A | 5/1989 | Pizziconi et al. | |
| 4,882,223 A | 11/1989 | Aptel et al. | |
| 4,935,141 A | 6/1990 | Buck et al. | |
| 4,950,224 A | 8/1990 | Gorsuch et al. | |
| 5,145,583 A | 9/1992 | Angleraud et al. | |
| 5,151,082 A | 9/1992 | Gorsuch et al. | |
| 5,152,743 A | 10/1992 | Gorsuch et al. | |
| 5,224,926 A | 7/1993 | Gorsuch et al. | |
| 5,605,627 A | 2/1997 | Carsen et al. | |
| 5,691,423 A * | 11/1997 | Smith et al. | 525/377 |
| 5,735,809 A | 4/1998 | Gorsuch et al. | |
| 5,980,478 A | 11/1999 | Gorsuch et al. | |
| 6,248,087 B1 * | 6/2001 | Spears et al. | 604/6.14 |
| 6,659,973 B2 * | 12/2003 | Gorsuch et al. | 604/6.04 |
| 6,802,971 B2 * | 10/2004 | Gorsuch et al. | 210/500.23 |
| 6,848,183 B2 * | 2/2005 | Lemisch | 30/153 |
| 6,899,692 B2 * | 5/2005 | Gorsuch et al. | 604/6.09 |
| 6,946,079 B1 * | 9/2005 | Holm | 210/749 |
| 7,195,711 B2 * | 3/2007 | Gorsuch et al. | 210/500.23 |
| 2002/0046970 A1 | 4/2002 | Murase et al. | |
| 2006/0106331 A1 * | 5/2006 | Gorsuch et al. | 604/6.09 |
| 2007/0023353 A1 * | 2/2007 | Gorsuch et al. | 210/500.23 |

FOREIGN PATENT DOCUMENTS

| | | |
|---|---|---|
| EP | 0801973 A1 | 10/1997 |
| EP | 0882494 A1 | 12/1998 |
| EP | 0998972 A | 5/2000 |
| FR | 2566003 A | 12/1985 |
| GB | 1374704 A | 11/1974 |
| JP | 9323031 A2 | 12/1997 |
| WO | WO 2004/009221 A | 1/2004 |

* cited by examiner

*Primary Examiner*—John Kim
(74) *Attorney, Agent, or Firm*—Knobbe Martens Olson & Bear LLP (57) ABSTRACT

An in-vivo plasmapheresis or in-vivo ultrafiltration membrane comprises a plurality of elongated hollow microporous fibers each fiber having an outer wall, an inner wall and an interior lumen extending along the length thereof and defined by an inner wall surface, and wherein the fiber wall structure is a substantially continuous change in mass density from the outer wall to the inner wall and comprises a continuum of voids bounded by solid frames, the fiber wall having an asymmetrical pore size and asymmetrical mass density between said inner wall surface and the outer wall surface with a higher mass density adjacent to the outer wall and a lower mass density adjacent to said inner wall, and characterized by a nitric oxide donor composition capable of producing or releasing nitric oxide or inducing nitric oxide production or release in-vivo with a blood vessel, distributed on or in the fiber wall.

39 Claims, 2 Drawing Sheets

ANTICOAGULANT AND THROMBO-RESISTANT HOLLOW FIBER MEMBRANES FOR IN-VIVO PLASMAPHERESIS AND ULTRAFILTRATION

CROSS-REFERENCE TO RELATED APPLICATIONS

This application is a continuation-in-part of application Ser. No. 10/959,918 filed Oct. 6, 2004, now U.S. Pat. No. 7,195,711, which is a continuation-in-part of application Ser. No. 10/666,185 filed Sep. 17, 2003, now U.S. Pat. No. 6,802,971, which is a divisional of application Ser. No. 09/549,131 filed Apr. 13, 2000, now U.S. Pat. No. 6,802,820.

BACKGROUND OF THE INVENTION

In U.S. Pat. Nos. 6,802,820 and 6,802,971 and application Ser. No. 10/959,918, now U.S. Pat. No. 7,195,711, there are described hollow fiber membranes capable of in-vivo plasmapheresis and/or in-vivo ultrafiltration. The aforesaid patents and application are incorporated herein by reference in their entirety, respectively. The described membranes comprise elongated hollow microporous fibers having an asymmetrical pore size and asymmetrical mass density between the inner and outer wall surfaces with a higher mass density adjacent to the outer wall and a lower mass density adjacent to the inner wall. The wall structure is also described as a continuous change in mass density between the outer fiber surface and the inner lumen surface with the pore size gradually changing between these inner and outer wall surfaces. The fibers are capable of separating blood plasma and toxins or metabolic waste from whole blood within a blood vessel by passing the plasma through the fiber wall from the outer wall surface to the interior lumen. The aforesaid asymmetrical hollow fiber membranes are used in filter devices to be implanted in the vasculature of a patient, such filter devices described in U.S. Pat. No. 6,899,692, incorporated by reference herein in its entirety. The use of such membranes and filter devices in apparatus and systems for therapeutic apheresis and patient fluid management are described in U.S. Pat. No. 6,849,183 and copending application Ser. No. 11/078,016, filed Mar. 11, 2005, now U.S. Pat. No. 7,481,936, both of which are incorporated by reference herein in their entirety, respectively.

During use, the relatively small pores at or adjacent to the outer fiber surface become clogged or occluded with particulate matter from the permeate (blood) whereby performance of the membranes is generally degraded over time. At least some of such clogging or fouling of the filter membranes is a result of blood clot formation (thrombosis) and platelet aggregation at the fiber surface. U.S. Pat. No. 6,659,973 is directed to apparatus and methods for periodically backflushing the hollow fibers to cleanse the membrane pores by removing the occlusions and restoring fiber performance. The description of the aforesaid '973 patent is incorporated by reference herein in its entirety. The backflush fluid may also be supplied with an anticoagulant such as heparin to assist in reducing blood clot formation and platelet aggregation at the fiber surface as described in copending application Ser. No. 10/408,657 filed Apr. 4, 2003, published as U.S. Patent Publication No. US-2003-0236482-A1 and now abandoned, also incorporated herein by reference. However, because the use of heparin in the backflush may increase the risk of bleeding, it may not be suitable for some patients.

SUMMARY OF THE INVENTION

The invention described herein comprises asymmetrical microporous hollow fiber membranes which may be implanted in a patient's blood vessel for carrying out in-vivo plasmapheresis and/or in-vivo ultrafiltration as previously described and which membranes are further characterized by a nitric oxide donor composition distributed on or in the fiber wall capable of releasing nitric oxide or inducing nitric oxide production or release in-vivo. The nitric oxide donor composition may be coated, embedded, impregnated, bonded, absorbed, immobilized or otherwise incorporated on or in the membrane fiber wall. Release of nitric oxide within the fiber wall or at the fiber wall surface exposed to blood in-vivo reduces thrombosis formation and pore fouling during plasmapheresis and/or ultrafiltration. In a preferred embodiment, the aforesaid fibers are used in a filter device comprising one or more elongated hollow tubes on which the fibers are secured.

DETAILED DESCRIPTION OF PREFERRED EMBODIMENTS

Figure 1:
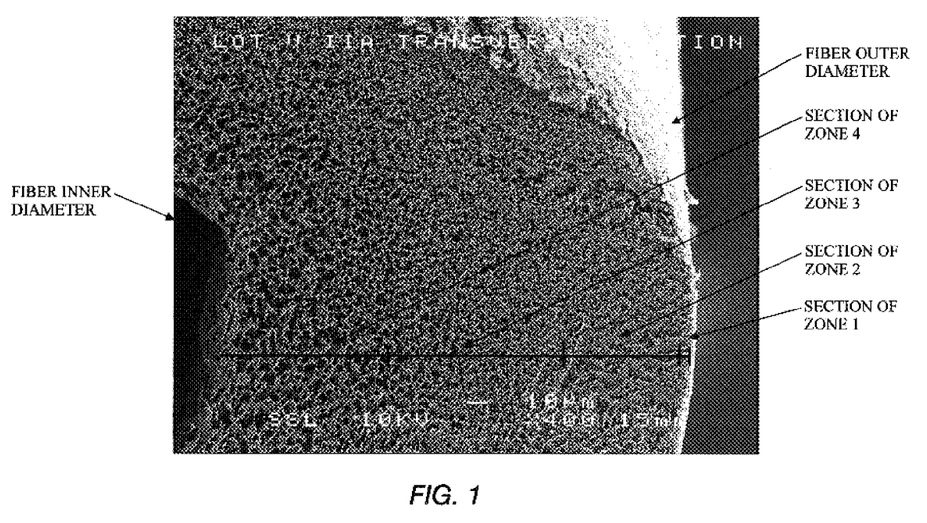
FIG. 1 is a scanning electron microscopy (SEM) image of a cross-section of a portion of a hollow microporous fiber membrane described herein at 400× magnification illustrating different zones of the asymmetrical wall structure between the inner and outer fiber wall surfaces.

As illustrated in FIG. 1, the features of the fiber wall of the membrane of the invention include a pore and void structure defined within frames or solid walls which form boundaries of the pores. The pores are voids of variable definitive sizes which permit passage of fluid through the fiber wall to the lumen and which pores obstruct the passage of components larger than the pore diameter. The pores are irregular-shaped voids bounded by solid frames to form irregular tortuous paths for irregular and regular-shaped solutes. The wall structure of the fiber from the outer surface to the lumen is a continuum with non-linear pore and void distribution. The resulting structure is a continuous change in mass density between the outer surface of the fiber and the inner lumen surface and whereby the pore size gradually changes between the fiber wall surfaces. The fiber wall illustrated is substantially without macrovoids. The fiber wall structure of the elongated microporous fibers is asymmetrical between the inner wall surface extending along the interior fiber lumen and the outer fiber wall surface exposed to blood in the blood vessel in which the filter device is implanted. The fiber wall at or adjacent to the outer wall surface has a higher mass density than the mass density adjacent to or at the inner wall surface at the fiber lumen. The mass density is a function of the average nominal pore size. FIG. 1 is a scanning electron microscopy (SEM) image of a cross-section of such a fiber at 400× magnification. It will be observed that the structure of the fiber from the outer surface to the lumen is a substantially continuous change in mass density whereby the pore size gradually changes between these fiber wall surfaces. It is convenient to describe the change in mass density as sections or zones of the wall area having an average nominal pore size, porosity and wall mass. The different mass density sections or zones of the wall area have an average nominal pore size range or average pore diameter range, each zone having a different average nominal pore size range. The walls may be characterized by two or more zones, for example 2, 3, or 4 or more mass density zones.

By way of example, the fiber wall illustrated in FIG. 1 may be described as having four zone sections, each zone characterized by a different mass pore density based on the average nominal pore size in the respective zones. The section of Zone 1 is adjacent to the fiber outer surface or outer diameter. Zone 1 forms the fiber interface with the permeate blood flow and, although being the thinnest zone, contains the highest density of operationally controlling pores for determining the fiber membrane performance and filtration characteristics, including the composition and components of separated plasma, and fiber membrane performance. Thus, Zone 1 has the principal effect in the filtration process for controlling the transmembrane flux (TMF) which is dependent on pore size, porosity and virtual membrane thickness. For plasmapheresis applications, preferred nominal average pore diameters in Zone 1 are between about 0.1 µm and about 1 µm, and more preferably range from about 0.4 µm to about 0.8 µm. A preferred filtration sizing has a cutoff of about 0.6 µm to about 0.8 µm. For ultrafiltration, Zone 1 nominal average pore diameters are between about 0.003 µm and about 0.006 µm. The membranes may also be described by reference to sieving coefficient cutoffs expressed in daltons. Preferred ultrafiltration membranes have sieving coefficient cutoffs between about $1 \times 10^4$ daltons and about $7 \times 10^4$ daltons, preferably below the molecular weight of albumin ($6.9 \times 10^4$ daltons) and more preferably between $3 \times 10^4$ daltons and $6.5 \times 10^4$ daltons.

Zones 2 and 3 are designed to decrease the flow path tortuosity and maintain the structural integrity required of the fiber exposed to physical conditions within the body. Pore size distribution in these zones may range gradually from about 0.8 µm to about 1.2 µm and from about 1.2 µm to about 2.5 µm, respectively. The section of Zone 2, while having some flux-controlling pores, is principally a structural member for providing strength to the fiber as well as acting as a conduit for exudate flow to the section of Zone 3. The latter is principally a structural member with expanded pores for reducing the hydraulic resistance and providing a fluid conduit to the lumen of the fiber, and thus, in the example, as shown, has little filtration function. Zone 4, representing the largest area having relatively large voids and pore diameters with little solid structure, has the primary function of a major reduction of hydraulic resistance through the membrane and defines the fiber inner lumen surface. Nominal average pore diameters in this lowest mass density zone are between about 1 µm and about 60 µm, and preferably between about 2 µm and about 6 µm. A typical fiber as shown has an OD of about 730±90 µm, an ID of about 230±70 µm and a wall thickness of about 245±75 µm. The pore sizes and zone dimensions given above are by way of example only.

The driving force for convective transport of the plasma and solutes across the membrane is the transmembrane flux (TMF) equal to $P_f \times$ transmembrane pressure (TMP and linear below the critical flow limit) where $P_f$ is the hydraulic permeability of the membrane, and:

$$P_f = (n\pi r_p^4)/(\tau\mu\Delta x)$$

where:
(n)=Porosity (number of pores/unit area)
(π)=3.14159
($r_p$)=Pore radius (pore size)
(τ)=Tortuosity of flow path
(µ)=Viscosity of solution
(Δx)=Membrane thickness The largest leverage to obtaining optimum TMF is the radius of the pores because it is raised to the fourth power, and thus the access fluid flow rate is increased exponentially. The next largest lever is the porosity or number of such pores/unit area. Thus, the exponential effect of the pore radius is multiplied by the porosity. Functional optimization for this application therefore also relies on achieving a tight standard deviation of pore radius in the effective zone of filtration as well as a high density of such pores in the primary filtration zone of the membrane. The relationship is also affected by temperature to the extent that temperature changes the value of the parameters including the viscosity of the solution.

The membranes described herein may be prepared using any suitable polymer which will result in a hollow fiber membrane which meets the required biocompatibility requirements and properties. Such membrane materials and surfaces must be highly biocompatible and resist clotting, protein adhesion and detrimental interaction with immune system components. The structural strength of the hollow fiber membranes must be high enough to safely withstand implantation as well as the hydraulic and physical perturbations existing in the vena cava environment. Thus, the functional convective or diffusive extraction efficiency of such hollow fibers must be suitable to meet clinical treatment requirements in the smallest possible size in order to fit within the vena cava without stress. The membranes also must be designed with a morphology capable of separating plasma from whole blood by filtering from the outside to the inside (lumen) of the fiber. A number of potentially suitable polymer fiber membrane materials include polyurethane, polypropylene, polysulfone, polyethersulfone, polycarbonate, nylon, polyimide, silicone, or other synthetic resins or combinations of two or more polymers known to those skilled in the art. A preferred polymer is polysulfone, and more preferably a polyethersulfone blended with polyethylene oxide and/or polyethylene glycol or a polysulfone modified with a polyethylene oxide-polyethylene glycol copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. The specific method used for producing the aforesaid polymers as well as the processes and parameters during the manufacture are known to those skilled in the art, for example, PCT Publication WO 90/04609.

An important characteristic of the fibers to be used in a filter device capable of being implanted in a patient's blood vessel and separating plasma from blood therein, is the ability to withstand the rigors and effects of implantation procedures, and to function efficiently and effectively in-vivo at the pressures and flows to which it is exposed. In addition to adequate tensile strength, relatively high elongation and breaking strength, as indicating the ability of the fiber to withstand the adverse conditions to which it is exposed, is of substantial importance. The fibers described herein are characterized by an average elongation breaking force strength of at least about 0.2 lbs. and preferably at least about 0.25 lbs., and an average elongation of at least about 45%, preferably above 60% and more preferably 65% or more. Such characteristics make the fibers especially suitable to meet in-vivo plasma filtration performance demands.

The nitric oxide donor composition incorporated in the microporous fiber comprises a source of nitric oxide capable of release in-vivo when the fiber membrane is exposed to blood within a patient's blood vessel. The nitric oxide donor composition may be coated, embedded, impregnated, bonded, absorbed, immobilized or otherwise distributed on or in the fiber wall. The nitric oxide donor composition may be incorporated on the primary membrane polymer, or it may be distributed on a secondary polymer composition which is distributed on or in the primary fiber polymer. Moreover, the nitric oxide releasing compound may be attached (bonded) to an atom of a polymer backbone, or attached to a group pendant to the polymer backbone, or it may be entrapped in the polymer matrix. Thus, the nitric oxide donor compounds may be distributed directly on or in the polysulfone or polyethersulfone which comprises the fiber wall polymer and/or the nitric oxide donor compound may be distributed on or in a secondary polymer which is distributed, coated, embedded, impregnated, absorbed or otherwise incorporated into and/or on the primary polymer fiber wall. The secondary polymer may be the same as the primary polymer or a different biocompatible polymer. Examples of different secondary polymers include biologically acceptable polyolefins, polyethyleneimine or derivatives, polyethers, polyesters, polyamides, polyurethanes and the like such as listed in PCT Publication WO 95/24908, incorporated herein by reference, and others known to those skilled in the art.

A preferred nitric oxide (NO) donor composition comprises a diazeniumdiolate, compounds with a N(O)NO group or $N_2O_2^-$ functional group that are also known as NONOates or NOC compounds. Examples of diazeniumdiolates include N-based diazeniumdiolates, C-based diazeniumdiolates, ionic diazeniumdiolates, O-derivatized diazeniumdiolates, and polymer-based diazeniumdiolates. The most common diazeniumdiolates are N-based diazeniumdiolates formed by the reaction of secondary amines and polyamines with NO under basic conditions. Such compounds are stable solids capable of regenerating two NO molecules with the starting amine in neutral or acidic buffers. Further description of such diazeniumdiolates and mechanisms for generation of such compounds are illustrated in Zhang et al., *Biomaterials* 23:1485-94, 2002, and other sources known to those skilled in the art.

Nitric oxide can also be generated or released from a polymer that is bound to a diazeniumdiolate group or a compound containing this group, as described in PCT Publication WO 95/24908, incorporated herein by reference. The polymer then may be coated on to the polysulfone or polyethersulfone fiber surface. The rate of NO release from the polymer can be modified by incorporating positively charged groups near the diazeniumdiolate group to inhibit the attack of positively charged $H^+$ ions on the diazeniumdiolate group. The polymer may contain a complex of a nucleophile (e.g., a primary amine, secondary amine, polyamine, or oxide) and a diazeniumdiolate group. Other complexes are described in the aforesaid publication.

Modified polypeptides and nucleic acids containing a diazeniumdiolate group as a NO donor may be incorporated into the fiber. The diazeniumdiolate group can be added to a nucleophile in the polypeptide or nucleic acid by exposing it to NO gas or the nucleophile can be added to the polypeptide or nucleic acid and then exposed to NO gas. Examples of such complexes are described in the aforesaid PCT Publication WO 95/24908 as well as WO 96/15797, incorporated herein by reference.

Modified polysaccharides may also be used as diazeniumdiolate NO donors. The diazeniumdiolate group can be covalently bound to the polysaccharide (such as by exposure of nucleophiles in the polysaccharide to NO gas) or can be associated with the polysaccharide through coprecipitation with a nucleophile/diazeniumdiolate complex. Examples of such complexes are described in the aforesaid WO 95/24908 PCT publication as are exemplary polysaccharides. Other disclosures of such compositions include PCT Publication WO 96/32136 and U.S. Pat. No. 5,691,423, incorporated herein by reference.

Another source of diazeniumdiolate NO donors are chitosan-based polymers. Modified chitosan polysaccharides containing a diazeniumdiolate group deliver NO, as described in PCT Publication WO 00/30658, incorporated herein by reference. Other polymers, e.g., plasticized polyvinylchlorides containing diazeniumdiolate groups may be prepared by dispersing one of the diazeniumdiolates-containing compounds such as described by Batchelor et al., *Journal of Medicinal Chemistry*, 2003, Vol. 46, No. 24, pp. 5153-61.

Catalysts capable of reducing endogenous NO donors, e.g., nitrites, nitrates or nitrosothiols may be absorbed or immobilized on the polysulfone or polyethersulfone membrane surface or on a secondary polymer distributed on the membrane surface to generate or release a local increase in NO level. Exemplary catalysts include enzymes such as mammalian xanthine oxidase or biomimetic catalysts such as copper (II)-ligand complexes that convert nitrite, nitrate or nitrosothiols to NO. Such catalysts are described in U.S. Patent Application Publication Nos. 2002/0115559 and 2004/0224868, both of which are incorporated herein by reference. To further increase the level of NO, salts of nitrite, nitrate or nitrosothiols may be doped with a polymer material or an underlying polymeric film to create a reservoir of NO donors that continuously leak into the immobilized catalytic layer.

Nitric oxide can also be generated or released from a polymer matrix with a reducible NO donor (e.g., a nitrosyl-containing organometallic compound such as sodium nitroprusside or an S-nitro compound such as S-nitrosoglutathione) and a reducing agent to convert the NO donor into NO. The rate of NO release may be regulated by varying the concentration of reductant included in the solid matrix. The matrix may be coated on the surface of the primary polysulfone or polyethersulfone of the asymmetric fiber wall, or coated on a secondary polymer which is then coated or distributed on the primary polymer. Examples of reductants and polymers are listed in PCT Publication WO 01/70199, incorporated herein by reference.

Other nitric oxide donor compositions include organic nitrates, organic nitrites, N-nitrosimines, nitrosothiols, C-nitroso compounds, furoxans, oxatriazole imines, oximines, sydnonimines, and others known to those skilled in the art such as listed by Wang, et al, *Chemical Reviews*, 2002, vol. 102, No. 4, pp 1091-1134.

Specifications and variation range of parameters for preferred hollow fiber membranes described herein for medical applications are as follows:

PLASMAPHERESIS APPLICATIONS

| PARAMETER | SPECIFICATIONS FROM | TO | RANGE OF APPLICATION FROM | TO |
|---|---|---|---|---|
| Outer Diameter μm | 640 | 820 | 200 | 1000 |
| Inner Diameter μm | 160 | 300 | 50 | 700 |
| Wall Thickness μm | 170 | 320 | 50 | 600 |
| Zone 1 mean flow pore diameter μm | 0.15 | 0.95 | 0.10 | 1 |
| Zone 4 pores @ ID diameter μm | 5 | 40 | 1 | 60 |
| Tensile force @ Break Pounds/in$^2$ | 600 | 1200 | 500 | 1500 |
| % Elongation @ Break | >45 | 100 | 45 | 150 |
| Elongation Break Strength (lbs. @ break) | >0.3 | 1.0 | 0.15 | 1.0 |
| Fluid Flux (H$_2$O) ml/min/cm$^2$ @ 100 mmHg | >1.0 | 12 | 1.0 | 30 |
| TMF plasma ml/min/cm$^2$/100 mmHg | >0.25 | 3 | .5 | 9 |

ULTRAFILTRATION APPLICATIONS

| PARAMETER | SPECIFICATIONS FROM | TO | RANGE OF APPLICATION FROM | TO |
|---|---|---|---|---|
| Outer Diameter μm | 640 | 820 | 200 | 1000 |
| Inner Diameter μm | 160 | 300 | 50 | 700 |
| Wall Thickness μm | 170 | 320 | 50 | 600 |
| Zone 1 mean flow pore diameter μm | 0.003 | 0.005 | 0.002 | 0.006 |
| Zone 4 pores @ ID diameter μm | 5 | 40 | 1 | 60 |
| TMF H$_2$O ml/min/cm$^2$/500 mmHg | 0.15 | 2 | 0.15 | 9 |
| Tensile force @ Break Pounds/in$^2$ | 600 | 1200 | 500 | 1500 |
| Elongation @ Break % | >45 | 100 | 45 | 150 |
| Elongation Break Strength (lbs. @ break) | >0.3 | 1.0 | 0.15 | 1.0 |

Figure 2:
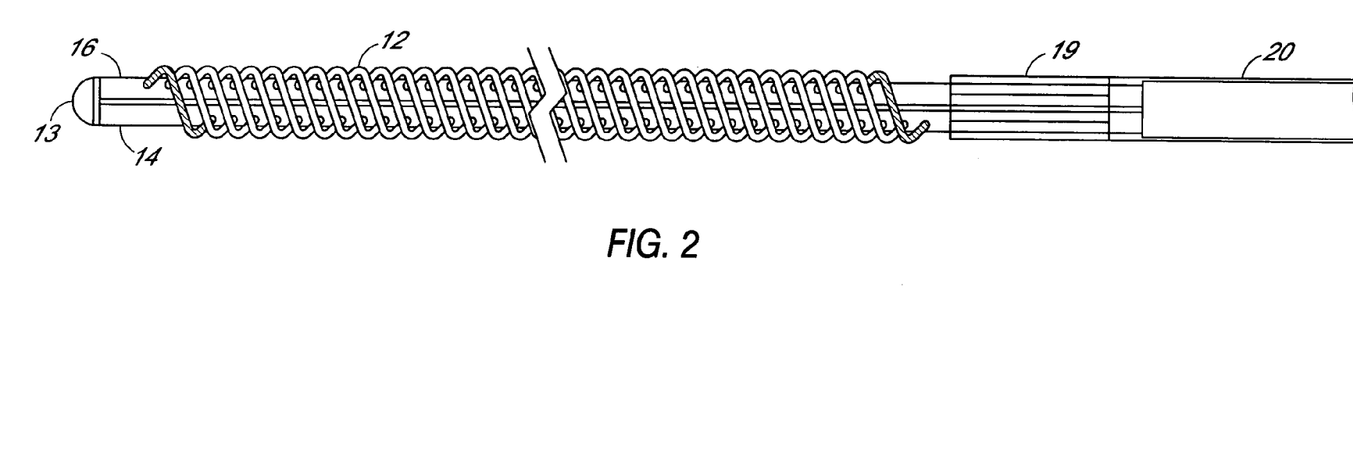
FIG. 2 shows a preferred embodiment of a filter device incorporating two elongated tubes on which the hollow fiber membranes are secured.

The above-described fibers are used in a filter device to be implanted in a patient for carrying out in-vivo plasmapheresis as described in the aforesaid patents and applications. A preferred filter device comprises one or more elongated hollow tubes to which the fibers are secured. In a preferred embodiment illustrated in FIG. 2, a pair of elongated hollow tubes are joined side-by-side lengthwise to form the core of the filter device. The two elongated hollow core tubes 14 and 16 terminate at a distal end with a distal end plug or cap 13 formed of a material that seals the open tube ends. The tubes and end cap may be made of any suitable biocompatible material, for example, medical grade extruded urethane tubes. Other biocompatible materials include synthetic rubbers, polycarbonate, polyethylene, polypropylene, nylon, etc. The elongated hollow tubes may be secured together using suitable bonding material 18, adhesive compositions, etc., for example, a UV curable adhesive applied along at least a portion of the tube surfaces. Alternatively, the tubes may be joined or connected by other means, for example, mating or interlocking shaped surfaces or interconnecting components. The tubes are secured to multiple lumen catheter 20 via a connector 19. The length and diameter of the filter device may be selected to accommodate the vessel or vein in which it is to be implanted. Examples of suitable tube lengths for human patients are between about 15 cm and about 25 cm, and preferably between about 18 cm and about 22 cm. Where a pair of core tubes is used as shown in the preferred embodiment, an outer diameter of each tube of between about 1 mm and about 3 mm is suitable. Although two tubes are shown in the embodiment illustrated, single tube embodiments may be used as described and shown in aforesaid Application Serial No. 11/078,016.

The fiber membranes described herein may be used in plasmapheresis filters and methods described in U.S. Pat. No. 6,899,692. Examples of medical applications for which the hollow fiber membranes of the present invention may be used include the following: therapeutic apheresis applications including plasma exchange, cascade protein separation by filtration, cascade protein removal or modification by adsorption cartridge, cryogenic modification, or chemical adaptation as described in U.S. Pat. No. 6,849,183, fluid management application such as described in aforesaid application Ser. No. 11/078,016 for congestive heart failure; tissue engineering applications including online generation of media for bioreactor from xenogeneic, allogeneic, or autologous sources as described in U.S. Pat. No. 6,607,501; continuous renal replacement therapy (CRRT) for both acute and chronic kidney failure; edema prevention therapies for MODS (multiple organ dysfunction syndrome) as described in U.S. Pat. No. 6,632,192; cytokine removal or modification in therapy for septic shock or SIRS (systemic inflammatory response syndrome); plasma extraction from peritoneal ascites; intermittent hemodialysis (IHD) or hemodiafiltration; and ARDS (acute respiratory distress syndrome) therapy by reduction of pulmonary edema and physiological pulmonary dead space. The descriptions of the aforesaid patents are incorporated herein in their entirety, respectively.

What is claimed is:

1. An in-vivo plasmapheresis or in-vivo ultrafiltration membrane comprising a plurality of elongated hollow microporous fibers each fiber having an outer wall, an inner wall and an interior lumen extending along the length thereof and defined by an inner wall surface, and wherein the fiber wall structure is a substantially continuous change in mass density from said outer wall to said inner wall and comprises a continuum of voids bounded by solid frames, said fiber wall having an asymmetrical pore size and asymmetrical mass density between said inner wall surface and the outer wall surface, said fiber wall having a higher mass density adjacent to the outer wall and a lower mass density adjacent to said inner wall, said fibers capable of separating blood plasma and toxins from whole blood within a blood vessel by passing the plasma and toxins through said fiber wall from the outer wall surface to the interior lumen, and a nitric oxide donor composition capable of generating or releasing nitric oxide or inducing nitric oxide production or release in-vivo within a blood vessel, distributed on or in said fiber wall.

2. A membrane of claim 1 wherein said nitric oxide donor composition is coated, embedded, impregnated, bonded, absorbed or immobilized on or in said fiber wall.

3. A membrane of claim 1 wherein said nitric oxide donor composition comprises a polymer composition having a nitric oxide donor coated, embedded, impregnated, bonded, absorbed or immobilized thereon.

4. A membrane of claim 2 wherein said microporous fibers comprise a primary polymer and wherein said nitric oxide donor composition comprises a secondary polymer having said nitric oxide donor coated, embedded, impregnated, bonded, absorbed, immobilized or otherwise distributed thereon or therein.

5. A membrane of claim 1 wherein said microporous fibers comprise a polysulfone.

6. A membrane of claim 1 wherein said microporous fibers comprise a polyethersulfone.

7. A membrane of claim 6 wherein said polyethersulfone is modified with polyethylene oxide and/or polyethylene glycol.

8. A membrane of claim 1 wherein said nitric oxide donor composition comprises a nitric oxide-releasing $N_2O_2^-$ functional group.

9. A membrane of claim 4 wherein said nitric oxide donor composition comprises a nitric oxide-releasing $N_2O_2^-$ functional group.

10. A membrane of claim 9 wherein said nitric oxide-releasing $N_2O_2^-$ functional group is bonded to said fiber wall.

11. A membrane of claim 6 wherein said nitric oxide donor composition comprises a nitric oxide-releasing $N_2O_2^-$ functional group.

12. A membrane of claim 11 wherein said nitric oxide-releasing $N_2O_2^-$ functional group is bonded to said fiber wall.

13. A membrane of claim 5 wherein said nitric oxide donor composition comprises a second polymer having a nitric oxide donor coated, embedded, impregnated, bonded or immobilized thereon.

14. A membrane of claim 6 wherein said nitric oxide donor composition comprises a second polymer having a nitric oxide donor coated, embedded, impregnated, bonded or immobilized thereon.

15. A membrane of claim 1 wherein said nitric oxide donor comprises a diazeniumdiolate.

16. A membrane of claim 5 wherein said nitric oxide donor comprises a diazeniumdiolate.

17. A membrane of claim 6 wherein said nitric oxide donor comprises a diazeniumdiolate.

18. A membrane of claim 8 wherein said nitric oxide donor comprises a diazeniumdiolate.

19. A membrane of claim 10 wherein said nitric oxide donor comprises a diazeniumdiolate.

20. A membrane of claim 13 wherein said nitric oxide donor comprises a diazeniumdiolate.

21. A membrane of claim 14 wherein said nitric oxide donor comprises a diazeniumdiolate.

22. A membrane of claim 1 wherein said nitric oxide donor composition comprises a catalyst capable of reducing endogenous NO donors in blood within a blood vessel.

23. A membrane of claim 5 wherein said nitric oxide donor composition comprises a catalyst capable of reducing endogenous NO donors in blood within a blood vessel.

24. A membrane of claim 6 wherein said nitric oxide donor composition comprises a catalyst capable of reducing endogenous NO donors in blood within a blood vessel.

25. A membrane of claim 22 wherein said microporous fibers comprise a polysulfone or polyethersulfone and wherein nitric oxide donor composition comprises a second polymer different from said polysulfone or polyethersulfone having said catalyst distributed therein.

26. A member of claim 25 wherein said catalyst comprises a xanthine oxidase or biomimetic catalyst.

27. A membrane of claim 1 wherein the higher mass density fiber wall is characterized by pores having a smaller average nominal pore size as compared to the average nominal pore size in the lower mass density fiber wall.

28. A membrane of claim 1 wherein said lower mass density is characterized by a nominal average pore diameter of between about 1 μm and about 60 μm.

29. A membrane of claim 1 wherein said higher mass density is characterized by a nominal average pore diameter of between about 0.10 μm and about 1 μm.

30. A membrane of claim 1 wherein said higher mass density is characterized by a nominal average pore diameter of between about 0.003 μm and about 0.006 μm.

31. A membrane of claim 1 having a sieving coefficient cutoff between about $1 \times 10^2$ daltons and about $7 \times 10^4$ daltons.

32. A membrane of claim 1 wherein said fibers have an average elongation breaking force strength of at least about 0.3 lbs. and an average elongation of at least about 45%.

33. A filter device for carrying out in-vivo plasma separation comprising one or more elongated hollow tubes and a plurality of elongated hollow microporous fibers each fiber having an outer wall, an inner wall and an interior lumen extending along the length thereof and defined by an inner wall surface, the ends of each fiber secured to said one or more tubes whereby the interior lumen of each fiber communicates with the interior of the one or more tubes, and wherein the fiber wall structure is a substantially continuous change in mass density from said outer wall to said inner wall and comprises a continuum of voids bounded by solid frames, said fiber wall having an asymmetrical pore size and asymmetrical mass density between said inner wall surface and the outer wall surface said fiber wall having a higher mass density adjacent to the outer wall and a lower mass density adjacent to said inner wall, said fibers capable of separating blood plasma and toxins from whole blood within a blood vessel by passing the plasma and toxins through said fiber wall from the outer wall surface to the interior lumen, and a nitric oxide donor composition capable of generating or releasing nitric oxide or inducing nitric oxide production or release in-vivo within a blood vessel, distributed on or in said fiber wall.

34. A filter device of claim 33 wherein said nitric oxide donor composition is coated, embedded, impregnated, bonded, absorbed or immobilized on or in said fiber wall.

35. A filter device of claim 33 wherein said nitric oxide donor composition comprises a polymer composition having a nitric oxide donor coated, embedded, impregnated, bonded, absorbed or immobilized thereon.

36. A filter device of claim 34 wherein said microporous fibers comprise a primary polymer and wherein said nitric oxide donor composition comprises a secondary polymer having said nitric oxide donor coated, embedded, impregnated, bonded, absorbed, immobilized or otherwise distributed thereon or therein.

37. A filter device of claim 33 wherein said microporous fibers comprise a polysulfone.

38. A filter device of claim 33 wherein said microporous fibers comprise a polyethersulfone.

39. A filter device of claim 38 wherein said polyethersulfone is modified with polyethylene oxide and/or polyethylene glycol.

* * * * *

UNITED STATES PATENT AND TRADEMARK OFFICE
CERTIFICATE OF CORRECTION

PATENT NO.        : 7,572,374 B2
APPLICATION NO.   : 11/334994
DATED             : August 11, 2009
INVENTOR(S)       : Gorsuch et al.

It is certified that error appears in the above-identified patent and that said Letters Patent is hereby corrected as shown below:

| Column | Line | 1. Description of Error |
|---|---|---|
| 5 | 57 | Change "$H^+ions$" to --$H^+$ ions--. |
| 9 | 57 | In Claim 26, change "member" to --membrane--. |
| 10 | 13 | In Claim 31, change "$1\times10^\infty$" to --$1\times10^4$--. |

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,572,374 B2 |
| APPLICATION NO. | : 11/334994 |
| DATED | : August 11, 2009 |
| INVENTOR(S) | : Gorsuch et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 859 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,572,374 B2  
APPLICATION NO. : 11/334994  
DATED : August 11, 2009  
INVENTOR(S) : Gorsuch et al.

Page 1 of 1

It is certified that error appears in the above-identified patent and that said Letters Patent is hereby corrected as shown below:

On the Title Page:

The first and sole Notice should read --

Subject to any disclaimer, the term of this patent is extended or adjusted under 35 U.S.C. 154(b) by 859 days.

Signed and Sealed this

Twenty-first Day of September, 2010

David J. Kappos
*Director of the United States Patent and Trademark Office*